Figure 1:
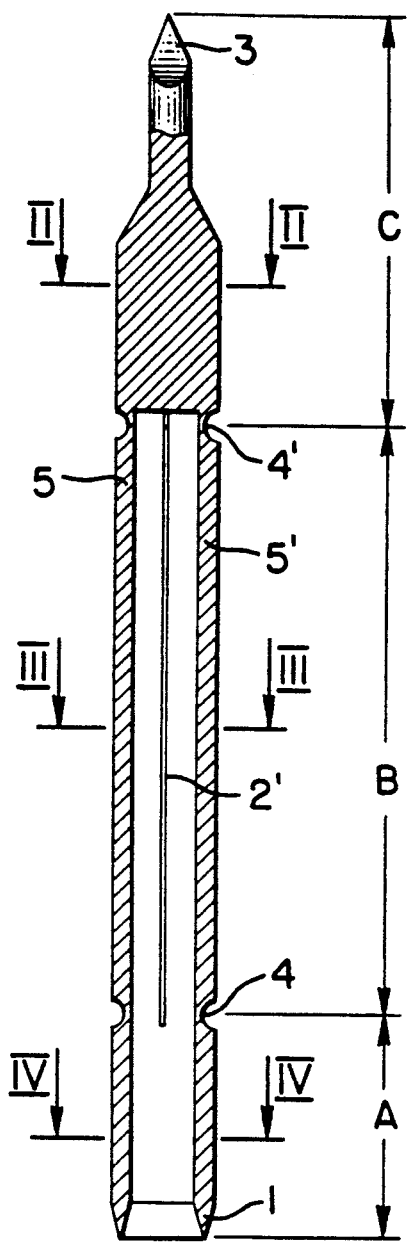

United States Patent [19]

Spitalny

[11] Patent Number: 5,269,316
[45] Date of Patent: Dec. 14, 1993

[54] SURGICAL INSTRUMENT

[76] Inventor: Hans-Henning Spitalny, Seestrasse 50, D-8210 Prien, Fed. Rep. of Germany

[21] Appl. No.: 931,049

[22] Filed: Aug. 17, 1992

[30] Foreign Application Priority Data

Aug. 16, 1991 [DE] Fed. Rep. of Germany ....... 4127166

[51] Int. Cl.⁵ .................................................. A61B 10/00
[52] U.S. Cl. ................................... 128/754; 128/749; 128/751; 606/167; 606/181; 606/184; 606/185
[58] Field of Search ................ 128/749, 751, 754, 753; 604/22; 606/79, 80, 167, 170, 180, 181, 184, 185

[56] References Cited

U.S. PATENT DOCUMENTS 3,913,566 10/1975 Lacey .................................. 128/754
4,022,191 5/1977 Jamshidi ............................. 128/753
5,055,105 10/1991 Hamlin et al. ....................... 606/80

Primary Examiner—C. Fred Rosenbaum
Assistant Examiner—Noelle Kent Cring
Attorney, Agent, or Firm—Felfe & Lynch

[57] ABSTRACT

A surgical instrument for the removal, transplantation or implantation of corium, fat, cartilage or alloplastic material is composed of three mutually severable adjacent sections, the first of which is a cylindrical hollow scalpel, the second is a hollow tube in communication with the hallow scalpel, and the third is made of solid material which is tapered to form a sharp needle. The tubular second section has longitudinally extending separating seams to permit its separation into two half shells after the first and third sections have been severed therefrom.

3 Claims, 5 Drawing Sheets

SURGICAL INSTRUMENT

FIELD OF THE INVENTION

This invention relates to a surgical instrument for the removal, transplantation or implantation of corium, fat, cartilage or alloplastic material.

BACKGROUND OF THE INVENTION

Normally, an appropriate section of tissue is obtained from the human or animal body by detaching the part due to undergo removal with a scalpel. Fatty tissue is frequently removed by means of a cannula attached to a vacuum pump or to a syringe.

These methods have various disadvantages. The removal of the tissue sample takes a great deal of time to perform and results in long scars which require follow-up treatment. Destroyed fat cells lead to oil cysts and subsequent histolysis which affects therapeutic success.

The prior art discloses various instruments for the removal of tissue samples. For example, German Offenlegungsschrift No. 40 04 934 discloses a tubular scalpel attached to a holder and provided with marks around the peripheral surfaces of the scalpel for the purpose of detecting the depth to which the scalpel has penetrated the skin. A ring-shaped adapter which is variable in length and is mounted on the tubular scalpel limits the depth of penetration.

German Offenlegungsschrift No. 21 03 918 discloses a hollow cylinder the front edge of which is shaped to form a cupped point, and the rear section of which merges into a handle which supports a pivoted detachable pressure plate at the end opposite the cupped point. The length of the instrument is dimensioned in such a way that the pressure plate is pressed against the operator's palm each time the handle is grasped by the thumb and index finger.

British Patent No. 1,474,175 discloses a device for the removal of skin grafts from the scalp for the purpose of transplanting hair. Following its removal, the skin graft is located inside the head of the tubular scalpel which may be motor-driven.

U.S. Pat. No. 3,561,449 discloses another device for transferring hair on the scalp from one location to another. This device consists essentially of a scalpel instrument and a handle, and describes in detail the way in which the scalpel head is attached to the handle.

Finally, U.S. Pat. No. 3,913,566 discloses an instrument which can be taken apart and is used especially for removing tissue samples which can be left in the scalpel section of the instrument. The scalpel section containing the tissue sample is then detached and stored in the handle and dispatched for further examination.

All of these prior art instruments are used only for removing tissue samples for biopsy at a vertical or right angle to the surface of the skin.

OBJECTS OF THE INVENTION

It is an object of the present invention to provide a surgical instrument which makes it possible to remove in a simple manner a piece of corium, fat or cartilage of sufficient length from a specific part of the body and, if necessary, to make the same available for immediate transplantation purposes.

Other objects of the present invention will become apparent as the description thereof proceeds.

DESCRIPTION OF THE INVENTION

Figure 2:
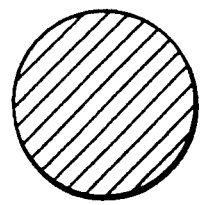
Figure 3:
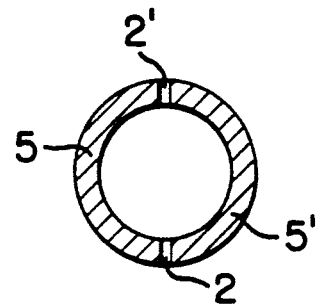
Figure 4:
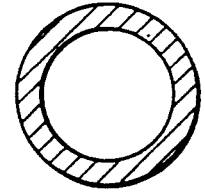
Figure 5:
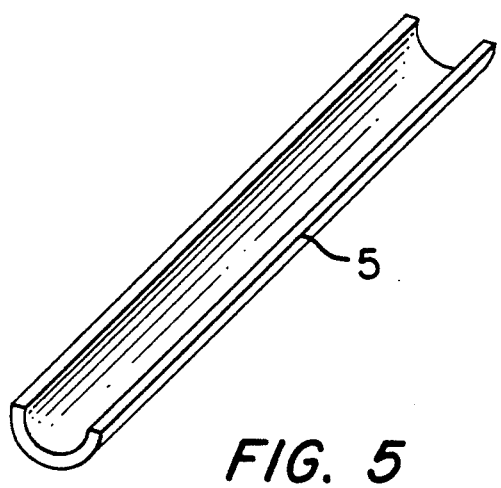
Figure 6A:
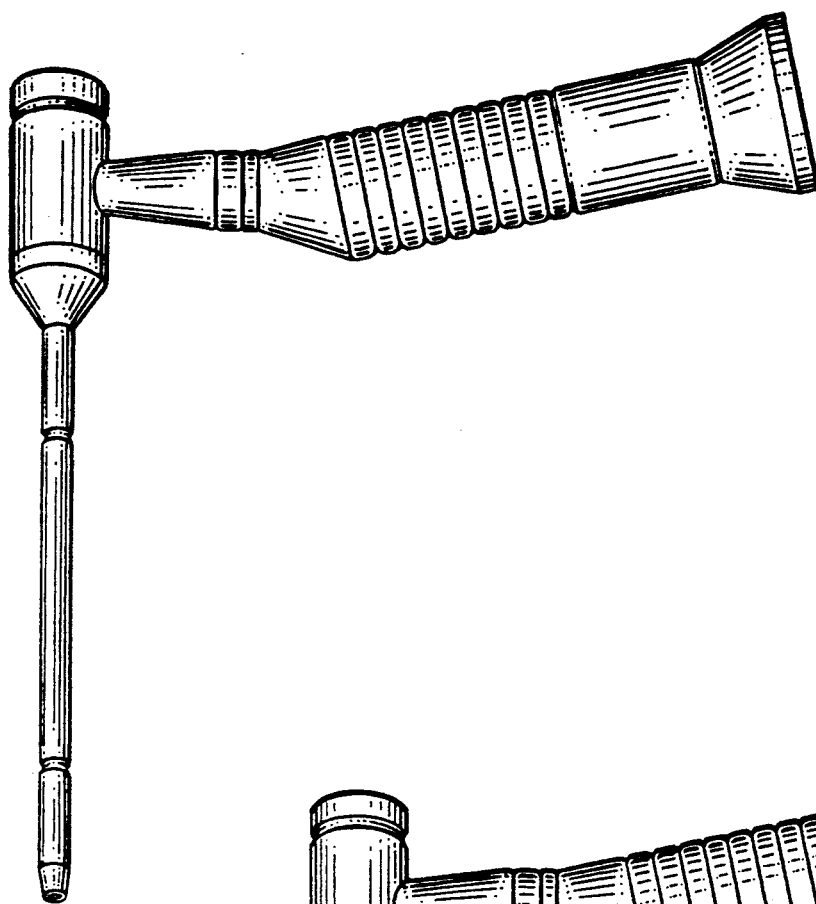
Figure 6B:
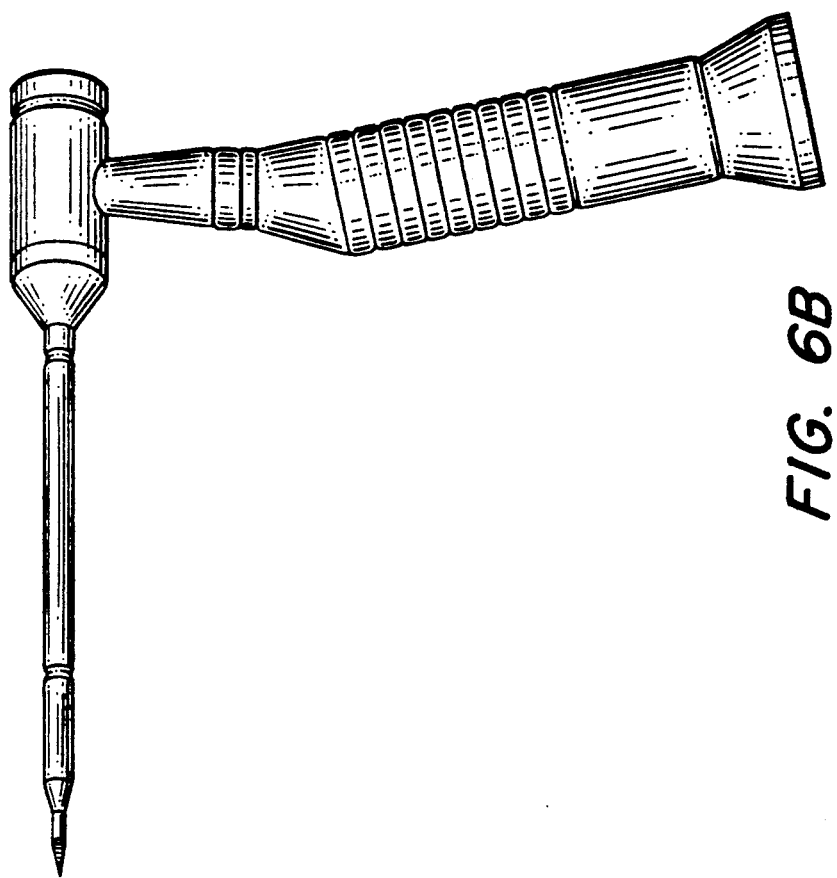
Figure 7:
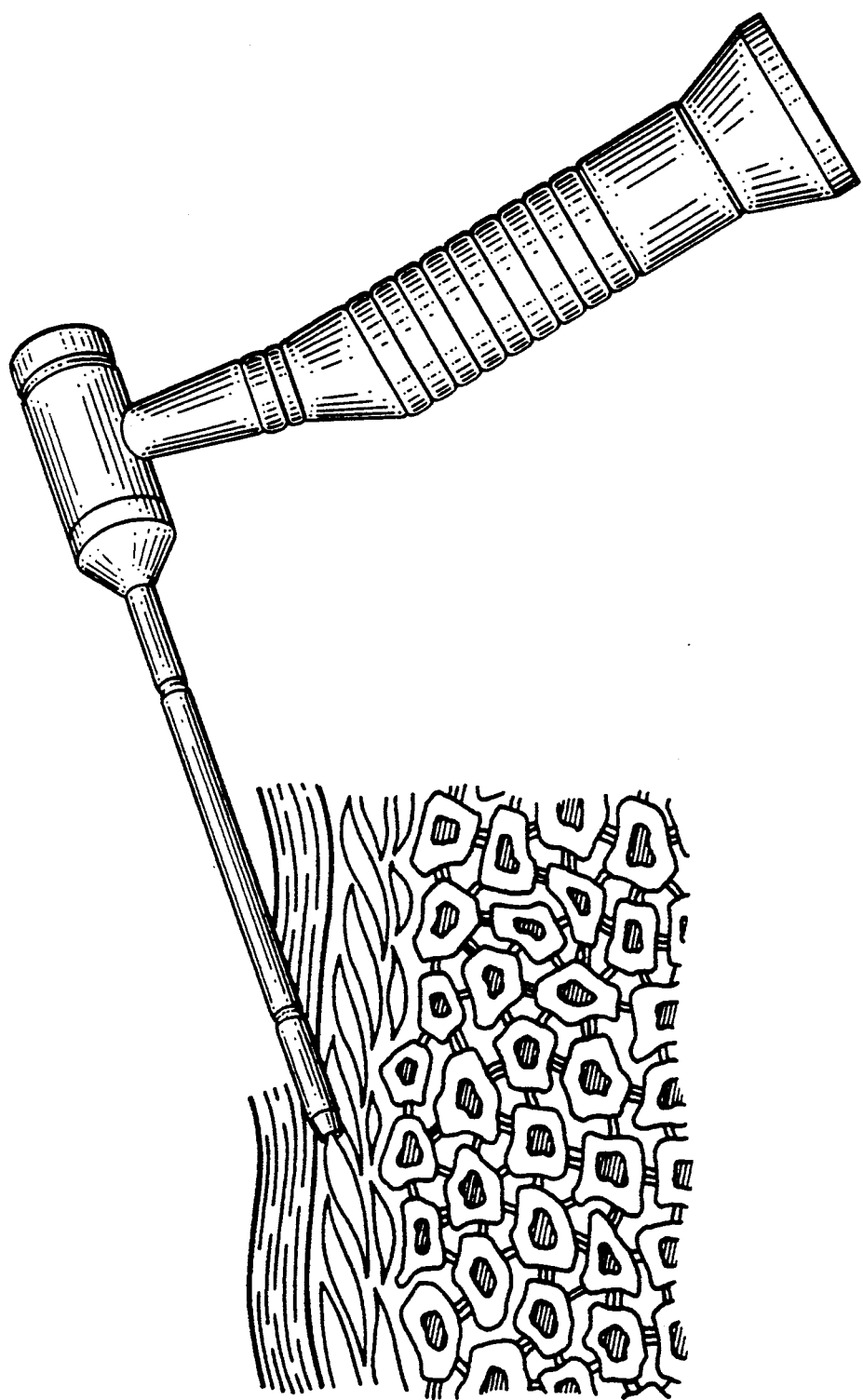
Figure 8:
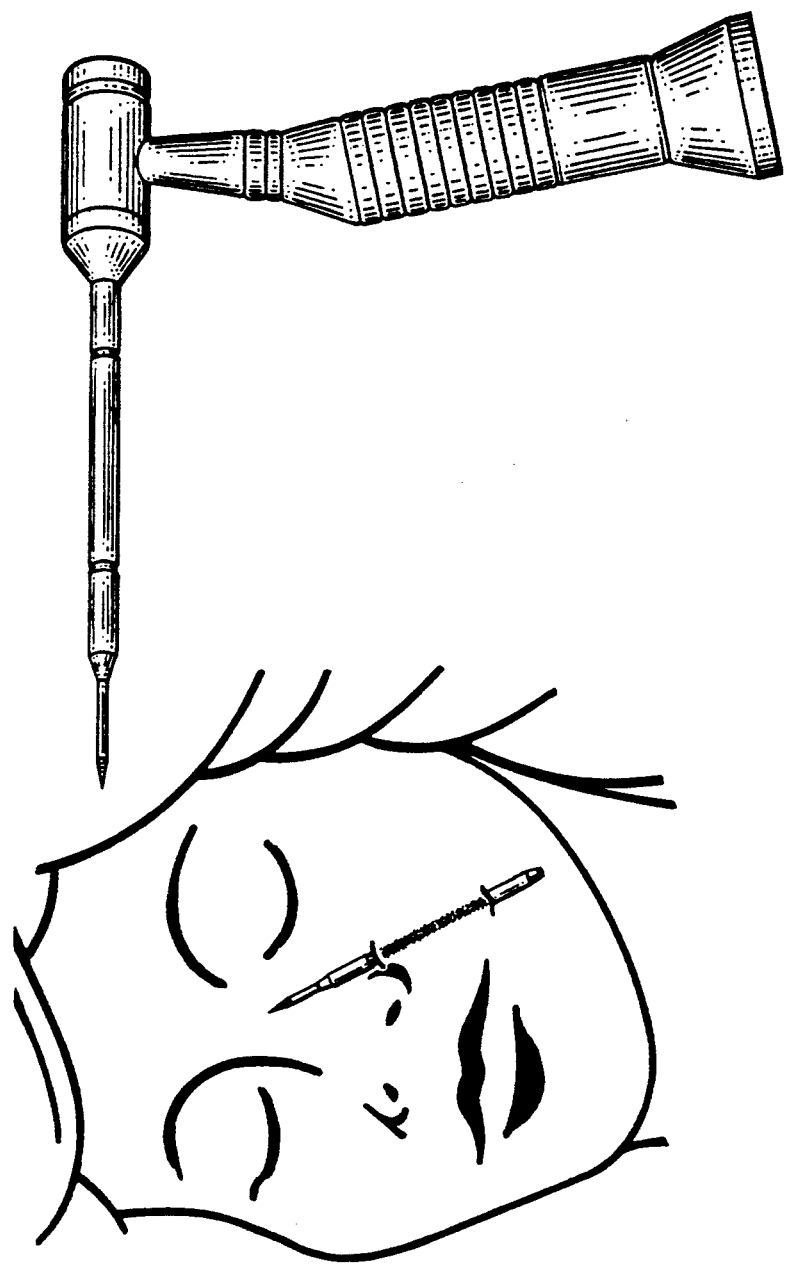
Figure 9:
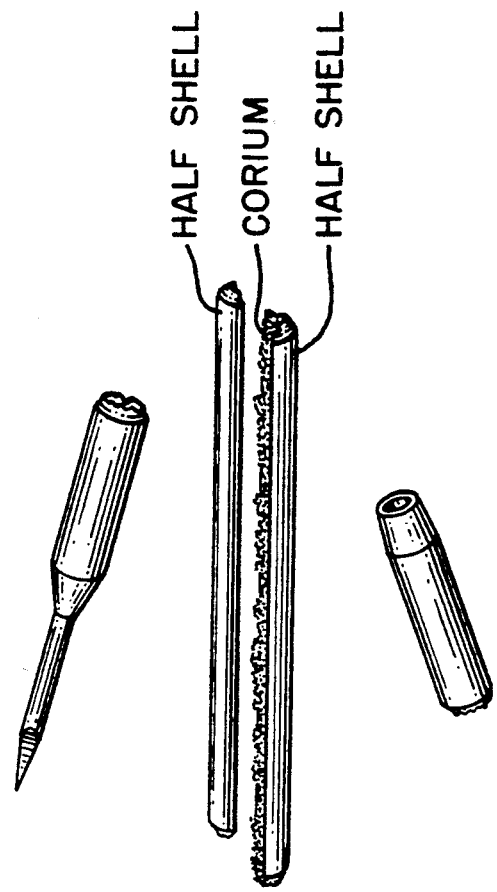
Figure 9:
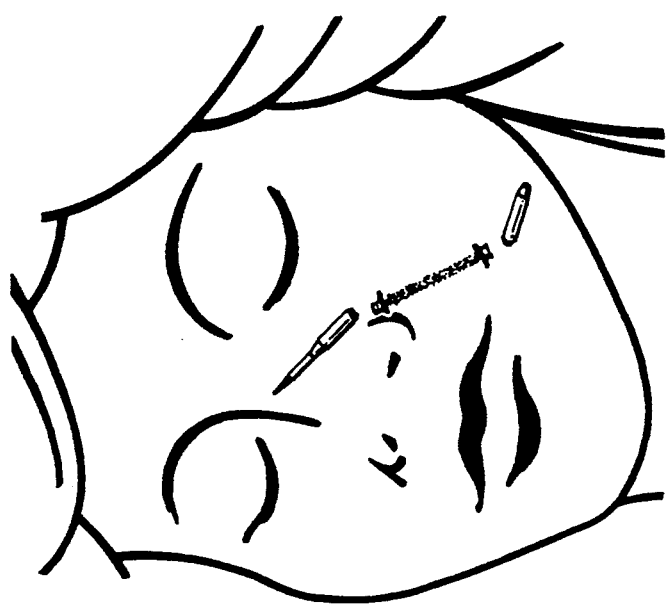

The above object is achieved in accordance with the present invention by means of the surgical instrument shown in the attached drawings of which FIG. 1 is a partial longitudinal section through the instrument, FIG. 2 is a transverse section along line II—II of FIG. 1, FIG. 3 is a transverse section along line III—III of FIG. 1, FIG. 4 is a transverse section along line IV—IV of FIG. 1, FIG. 5 is a perspective view of a portion of section B of the instrument, FIG. 6A is a perspective view of section A of the instrument inserted into a surgical drill, FIG. 6B is a perspective view of section C of the instrument inserted into a surgical drill, FIG. 7 shows how the instrument is used to obtain a specimen of corium for transplantation, FIG. 8 shows how the instrument containing corium is inserted under the skin for transplantation, and FIG. 9 shows how sections A and C are broken off and the transplantation of corium is completed.

Referring now to FIG. 1 of the drawings, the surgical instrument of the present invention consists essentially of a cannula open on one end comprising three sections A, B and C rigidly joined to one another. Section A is tubular in shape and designed in the form of a scalpel device. Its open end (1) is sharpened, and the other end is marked by an annular notch (4) in the wall of the cannula. The open, sharpened end (1) is preferably provided with a cylindrical edge. By means of a surgical drill into which the instrument can be inserted with its section A (FIG. 6A) or with its section C (FIG. 6B), it is made to rotate, thus being ready for cutting or drilling in order to sever the epidermis at the donor removal point. The advancement of the cannula takes place parallel to the surface of the skin.

The centrally located section B of the instrument consists of one or several channels or shells rigidly connected to sections A and C, respectively. Section B is formed as a result of the end of section B that is situated opposite Section A likewise marked with an annular notch 4' and comprising two or more separating seams 2 and 2' (FIG. 3) extending over the entire length of section B parallel to the longitudinal axis of the cannula in the walls thereof. Section B preferably comprises two separating seams 2 and 2' situated on opposite sides, resulting in two half shells 5 (FIG. 5) being formed. The separating seams between the half shells 5 and 5' are 0 to 0.5 mm wide. After the instrument has fully advanced, the tissue sample extracted in cylindrical form will be located between the shells 5 and 5'. After sections A and C are broken off at annular notches 4 and 4', after the instrument has been appropriately introduced into the skin at one point and withdrawn again at another point, section B remains in the form of one or more shells separated from one another (FIG. 5) below the surface of the skin of the treated part of the body. Section C of the instrument is constructed of solid material and tapers to form a pyramidal or conical sharpened needle 3.

The transition points from section A to B and from section B to C, respectively, are marked by annular notches 4 and 4' in the wall of the cannula. The purpose of these notches is to indicate the end of the scalpel section A, the middle section B and section C which is made of solid material. These notches assume the form of rectangular, wedge-shaped, square or semicircular recesses in the wall of the cannula and provide the predetermined breaking points as a result of cross-sectional reduction. Prior to removal of the instruments from the skin, sections A and B are broken off, so that only the tissue-filled shells 5 and 5' forming the middle section B remain. By slight radial lifting and axial removal of the individual shell segments, the tissue located between the shells remains in the introduced position and is merely smoothed by trimming the ends.

FIGS. 2 through 4 are, as indicated above, cross sections of the surgical instrument at various points thereof. FIG. 5 is a perspective view of a half shell of the instrument after sections A and C have been broken off.

The length of the various sections of the instrument are as follows: section A—5 to 20 mm; section B—20 to 150 mm; section C—10 to 50 mm. The preferred length of the various sections are the following: A—2 cm; B—10 cm; and C—2 cm.

Depending upon the intended use and the nature of the tissue to be removed, the inside diameter of the cannula may be from 1 to 20 mm. In general, a cannula the inside diameter of which is 1.5 mm is sufficient for performing skin transplantations.

The width of the separation seams with 2 and 2' which extend parallel to the axis of the cannula and form the shells of the middle section B as shown in FIG. 5, may be 0 to 0.5 mm, depending on the intended use of the instrument.

Besides being useful for the removal and transplantation of endogenic tissue, such as corium, fat or cartilage, the instrument according to the present invention can also be employed for implanting foreign substances, that is, alloplastic material such as collagens or silicone. Thus, by introducing the instrument beneath the skin of the body parts undergoing treatment, exact placement of the material is possible.

The instrument is preferably constructed of stainless materials, such as stainless steel, titanium, glass or plastic.

The following is an example of how the instrument of the present invention is used for the transplantation of corium.

Section C of the instrument is clamped into the chuck of a surgical drill (FIG. 6B). After a local anesthetic has been given at a point where corium is as thick as possible, preferably in the lateral gluteal region, and following a minimal stab incision, the instrument is advanced at low speed closely beneath the epithelium parallel to the surface of the skin (FIG. 7). The corium is excised without epithelium and fat and is deposited inside the lumen of the instrument. After sufficient corium has been deposited, the instrument is then ejected through the epithelium. The transplantation instrument containing the corium in the lumen is now removed from the drill chuck and withdrawn from the hypodermis. The material present inside the lumen of the instrument can, if desired, be compacted with either a mandrin or a larding bore needle, and the process can be repeated. In this way more material is obtained which is also compressed inside the lumen.

For implantation of the recovered lumen, section A of the instrument is clamped into the chuck of the surgical drill (FIG. 6A). Following disinfection, the fold or scar undergoing treatment is provided with a local anesthetic, and the tip of section C of the instrument enters the skin at the point where the fold or defect commences (FIG. 8). With the tip C rotating at low speed, the dense fibrous tissue is loosened from the terminal muscle fibers that merge into the depth of the fold. At the end of the fold the epidermis is pierced again from underneath to emerge above the skin. The drill is then disconnected from the instrument. The predetermined breaking points, that is, annular notches 4 and 4', are located outside the epidermis at both the entry and exit points of the drilling channel (FIG. 8). Sections A and C of the instrument are now broken off at the predetermined breaking points 4 and 4' using the fingers or two clamps (FIG. 9). The exposed half shells of section B are easily removable, leaving the implanted corium in place.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. A surgical instrument for the removal, transplantation of implantation or corium, fat, cartilage or alloplastic material consisting of a cannula having a pair of spaced-apart circumferential grooves formed therein, said grooves defining three mutually severable adjacent sections of which the first section is in tubular form having a sharpened open end defining a scalpel, the second section is in tubular form in communication with said first section and having at least two separating seams extending parallel to the axis of the cannula over the entire length of said second section to permit separation of said second section into two half shells, and the third section consists of solid material tapered to form a sharp needle.

2. A surgical instrument of claim 1, wherein the scalpel end of said first section is cylindrically sharpened.

3. A surgical instrument of claim 1 made of stainless steel.

* * * * *